United States Patent
Pletcher et al.

(10) Patent No.: US 10,832,804 B2
(45) Date of Patent: *Nov. 10, 2020

(54) METHOD AND PROCESS FOR TRANSPORTING HEALTH INFORMATION

(71) Applicant: Michigan Health Information Network Shared Services, East Lansing, MI (US)

(72) Inventors: Tim Pletcher, Mount Pleasant, MI (US); Jeff Livesay, Winston-Salem, NC (US); Rod Mach, Northville, MI (US)

(73) Assignee: Michigan Health Information Network Shared Services, East Lansing, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 16/182,559

(22) Filed: Nov. 6, 2018

(65) Prior Publication Data

US 2019/0080042 A1 Mar. 14, 2019

Related U.S. Application Data

(63) Continuation of application No. 15/081,186, filed on Mar. 25, 2016, now Pat. No. 10,120,978, which is a continuation of application No. 14/486,068, filed on Sep. 15, 2014, now Pat. No. 10,311,203.

(60) Provisional application No. 61/877,708, filed on Sep. 13, 2013.

(51) Int. Cl.
*G16H 10/60* (2018.01)
*G06F 19/00* (2018.01)

(52) U.S. Cl.
CPC ............ *G16H 10/60* (2018.01); *G06F 19/00* (2013.01)

(58) Field of Classification Search
None
See application file for complete search history.

(56) References Cited

U.S. PATENT DOCUMENTS

| | | |
|---|---|---|
| 7,752,035 B2 | 7/2010 | Oon |
| 7,890,748 B1 | 2/2011 | Wyatt |
| 8,285,565 B2 | 10/2012 | Kerr et al. |
| 8,311,855 B2 | 11/2012 | Kerr et al. |
| 8,473,308 B2 | 6/2013 | Fackler et al. |
| 10,120,978 B2 | 11/2018 | Pletcher et al. |
| 2002/0016923 A1 | 2/2002 | Knaus et al. |
| 2005/0119917 A1 | 6/2005 | Kim |
| 2005/0228808 A1 | 10/2005 | Mamou et al. |
| 2005/0236474 A1 | 10/2005 | Onuma et al. |

(Continued)

FOREIGN PATENT DOCUMENTS

| | | |
|---|---|---|
| WO | WO-2010/135578 A2 | 11/2010 |
| WO | WO-2011/011540 A2 | 1/2011 |
| WO | WO-2013/097905 A1 | 7/2013 |

*Primary Examiner* — Linh Giang Le
(74) *Attorney, Agent, or Firm* — Honigman LLP

(57) ABSTRACT

A method for transforming and transporting health information is disclosed herein. The method includes receiving the health information; transforming the received health information of based on a predetermined rule; validating whether the received health information is in a proper form based on a third-party standard; and parsing the de-identified received health information to determine an entity to receive the de-identified health information.

20 Claims, 7 Drawing Sheets

(56) References Cited

U.S. PATENT DOCUMENTS

| | | |
|---|---|---|
| 2007/0061393 A1* | 3/2007 | Moore .................. G06F 19/325 |
| | | 709/201 |
| 2008/0010091 A1 | 1/2008 | Kim et al. |
| 2008/0021732 A1 | 1/2008 | Richards et al. |
| 2008/0046292 A1 | 2/2008 | Myers et al. |
| 2008/0195421 A1 | 8/2008 | Ludwig et al. |
| 2008/0270180 A1 | 10/2008 | Sholtis et al. |
| 2010/0082371 A1 | 4/2010 | Kamp et al. |
| 2010/0088117 A1 | 4/2010 | Belden et al. |
| 2010/0191546 A1 | 7/2010 | Kanamarlapudi et al. |
| 2011/0119088 A1 | 5/2011 | Gunn |
| 2011/0119089 A1 | 5/2011 | Carlisle |
| 2011/0119092 A1 | 5/2011 | Szela, Jr. et al. |
| 2012/0232929 A1 | 9/2012 | Experton |
| 2012/0239413 A1 | 9/2012 | Mathur et al. |
| 2012/0253842 A1 | 10/2012 | Curran et al. |
| 2013/0054613 A1 | 2/2013 | Bishop |
| 2014/0039912 A1 | 2/2014 | Turinas et al. |
| 2015/0081325 A1 | 3/2015 | Pletcher et al. |

\* cited by examiner

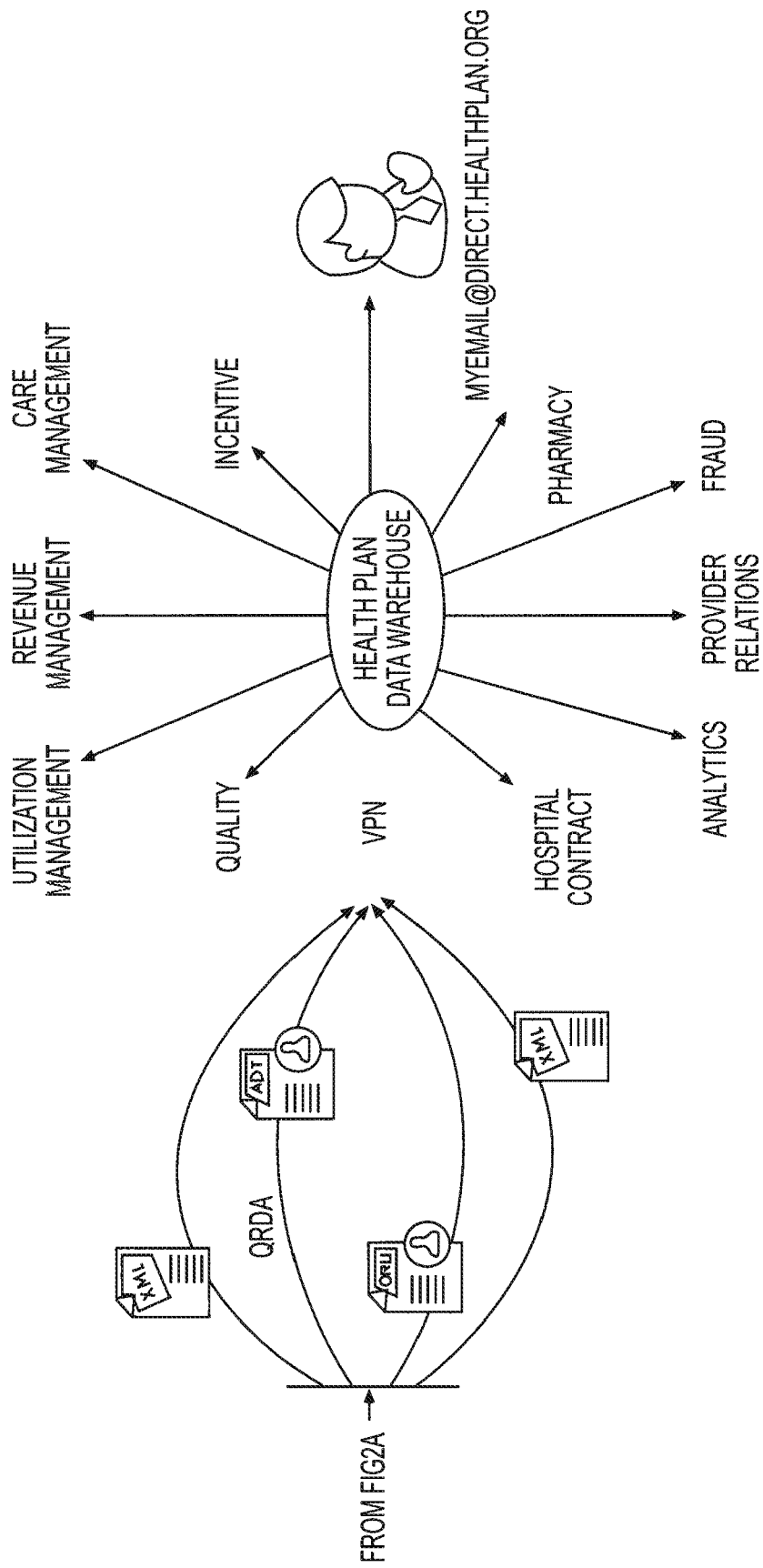
FIG. 2A-CONT

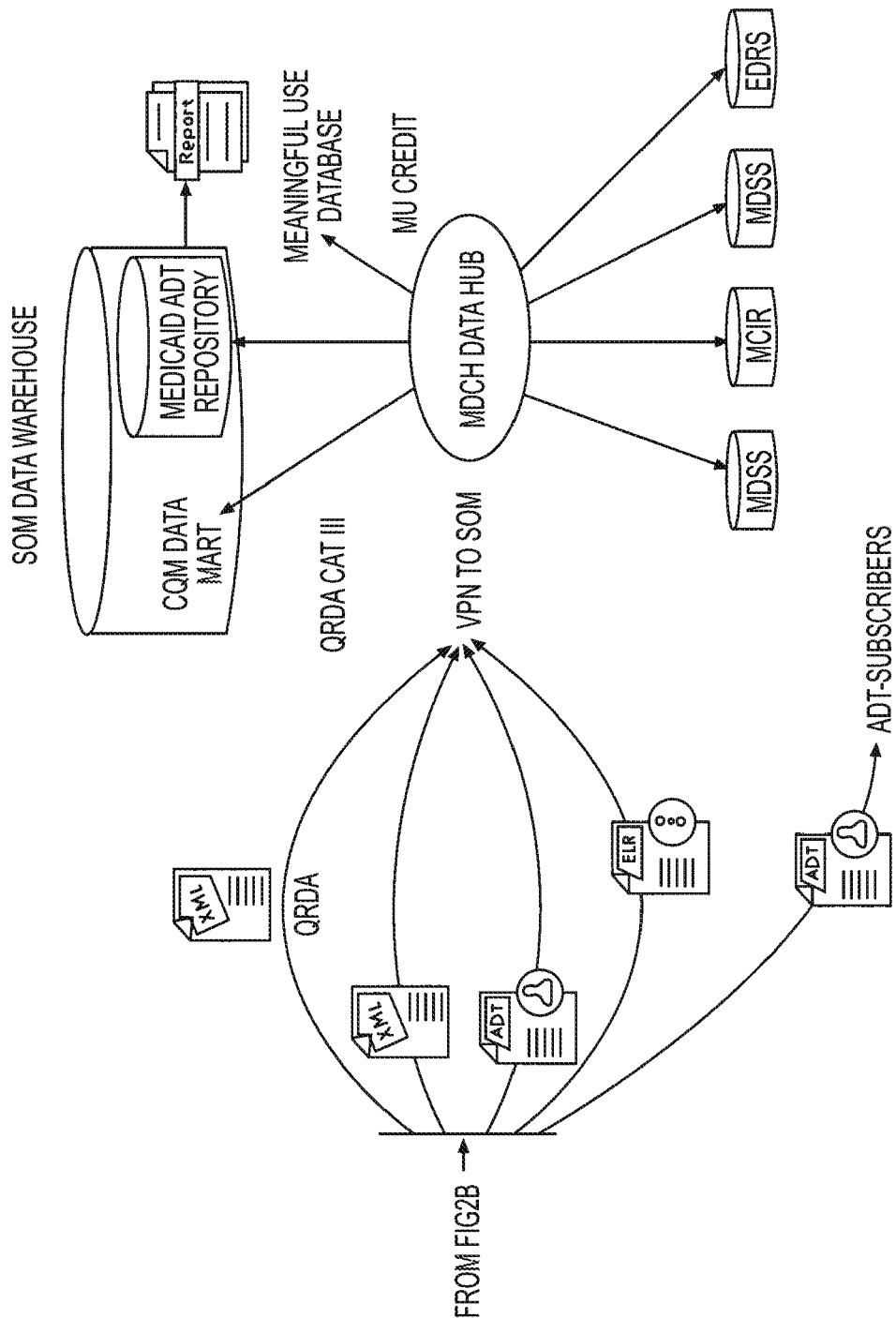
FIG. 2B-CONT

METHOD AND PROCESS FOR TRANSPORTING HEALTH INFORMATION

CROSS REFERENCE TO RELATED APPLICATIONS

This application is a continuation of and claims the benefit of U.S. patent application Ser. No. 15/081,186, filed Mar. 25, 2016, which is a continuation application of and claims the benefit of U.S. patent application Ser. No. 14/486,068, filed Sep. 15, 2014 which claims the benefit of U.S. Provisional Patent Application No. 61/877,708, filed Sep. 13, 2013, the entire disclosures of the applications being considered part of the disclosure of this application and are hereby incorporated by reference.

BACKGROUND

In various industries and organizations, the parties that provide and receive services may communicate with each other. Often times, communication is performed via paper or a non-electronic media. For example, the parties may communicate to each other via mail or fax.

With the advent of networks, such as the Internet, the parties may communicate with each other through electronic media. For example, one party may communicate information to another party via electronic mail (email). In another example, one party may maintain storage, and allow visiting parties to access the storage via a retrieving protocol, such as a File Transfer Protocol (FTP).

In certain industries, for example health care, certain precautions may be required when parties share information with each other. Some of these precautions may be mandated or required by federal laws or regulations. In particular, statutes may dictate that when information is passed from one party to another (i.e. a first health care provider to a second health care provider), that certain security and privacy concerns are maintained through protective techniques such as encryption to reduce the likelihood of security breaches and violations of privacy regulations through the disclosure of personal health information (PHI).

The Office of the National Coordinator (ONC) established the Direct Project which defines a standard protocol for secure messaging by email. The Direct protocol allows participants to send authenticated, secure messages containing encrypted health information to known, trusted recipients over the Internet. In essence, the Direct protocol creates a closed network where only verified and trusted participants may communicate with each other. The Direct protocol employs the use of secure Simple Mail Transfer Protocol (SMTP) to facilitate the sending of messages from one party to another and requires special digital security certificates for the encryption/decryption.

Each provider that shares health information may be registered with a Health Information Service Provider (HISP) that is similar to an Internet Service Provider (ISP) but that specializes in Direct secure messaging (secure email). One HISP may service many health care entities. Additionally, several HISPs may be established, and communication between HISPs may be performed employing a closed network messaging protocol, such as Direct. Each health care entity may have a unique identifier granted by one of the HISPs, and use the identifiers to communicate with one another (for example, 'physicianX@direct.hospitalA.org').

An example of communicating with a closed network such as one that employs the Direct protocol is described below. The sender pushes the message from the sender's HISP to the receiver's HISP. In this case, the sender may be a general physician who wants to transmit health information to a specialist.

The sender's HISP may communicate securely with the receiver's HISP if the two HISPs have established a trust anchor by exchanging digital security certificates. The sender's HISP may refer to a routing information directory and push the message to the receiver's HISP accordingly.

In the final stage, the receiver's HISP may receive the encrypted message and provide the message in unencrypted form to the recipient. Thus, through communicating with closed messaging, such as employing the Direct protocol, a first health care provider may securely and electronically transmit health information to an authenticated second health care provider. In this way, due to the messaging occurring electronically, a more efficient delivery of health information is achieved in a secure way.

The above example describes a situation in which one physician is communicating with another physician. One of ordinary skill in the art may appreciate that the above described messaging may occur with various parties, such as clinics, patients, testing labs, and the like.

The Direct Project and Direct standard also allows for system endpoints (i.e. an automated sender or an automated receiver) such that the following communications are possible using Direct:

| Sender | Receiver |
| --- | --- |
| Person | Person |
| Person | System |
| System | Person |
| System | System |

The legislated name under the Affordable Care Act for a Direct secure email address is "Electronic Service Information" or ESI. Utilization of Direct by healthcare providers is mandated under the Affordable Care Act for Meaningful Use Stage Two, which under the present Act is required by January 2014. As a result, Direct secure email accounts are becoming a widely available commodity as numerous vendors drive the costs out of operating a Direct HISP.

SUMMARY

A method for transforming and transporting health information is disclosed herein. The method includes receiving the health information; transforming the received health information of based on a predetermined rule; validating whether the received health information is in a proper form based on a third-party standard; and parsing the de-identified received health information to determine an entity to receive the de-identified health information.

DESCRIPTION OF THE DRAWINGS

The detailed description refers to the following drawings, in which like numerals refer to like items, and in which.

DETAILED DESCRIPTION

Electronic document sharing, especially in certain fields such as health care, may mandate or prefer that precautions be taken to ensure privacy when health information is shared. In healthcare two mandates affecting health information are required by federal statute, the Health Information Portability and Accountability Act (HIPAA) and the Health Information Technology for Economic and Clinical Health Act (HITECH) Act. Thus, various health care services, providers and stakeholders may be required to implement processes and methods that ensure that information is secure.

Disclosed herein are methods and processes for securely transporting health information. Further methods and processes disclosed herein are related to downloading, detaching ("peeling"), streaming, validating and routing health information. By providing the methods and systems disclosed herein, the transformation and secure transportation of health information may be enabled more easily and made more efficient.

Further, because of the aspects disclosed herein, certain steps necessary for public health surveillance, de-identification, substitution, validation, error correction and other data manipulation may be automated as well. Through the methods disclosed herein, the burden of accomplishing the above-enumerated tasks is removed from each HISP, and the secure transport of health information may occur seamlessly, at low cost, and with minimal effort. All of the transformation and secure transport of health information may be performed while ensuring that various mandated regulations and policy goals are maintained and achieved by the methods and processes disclosed herein.

Figure 1:
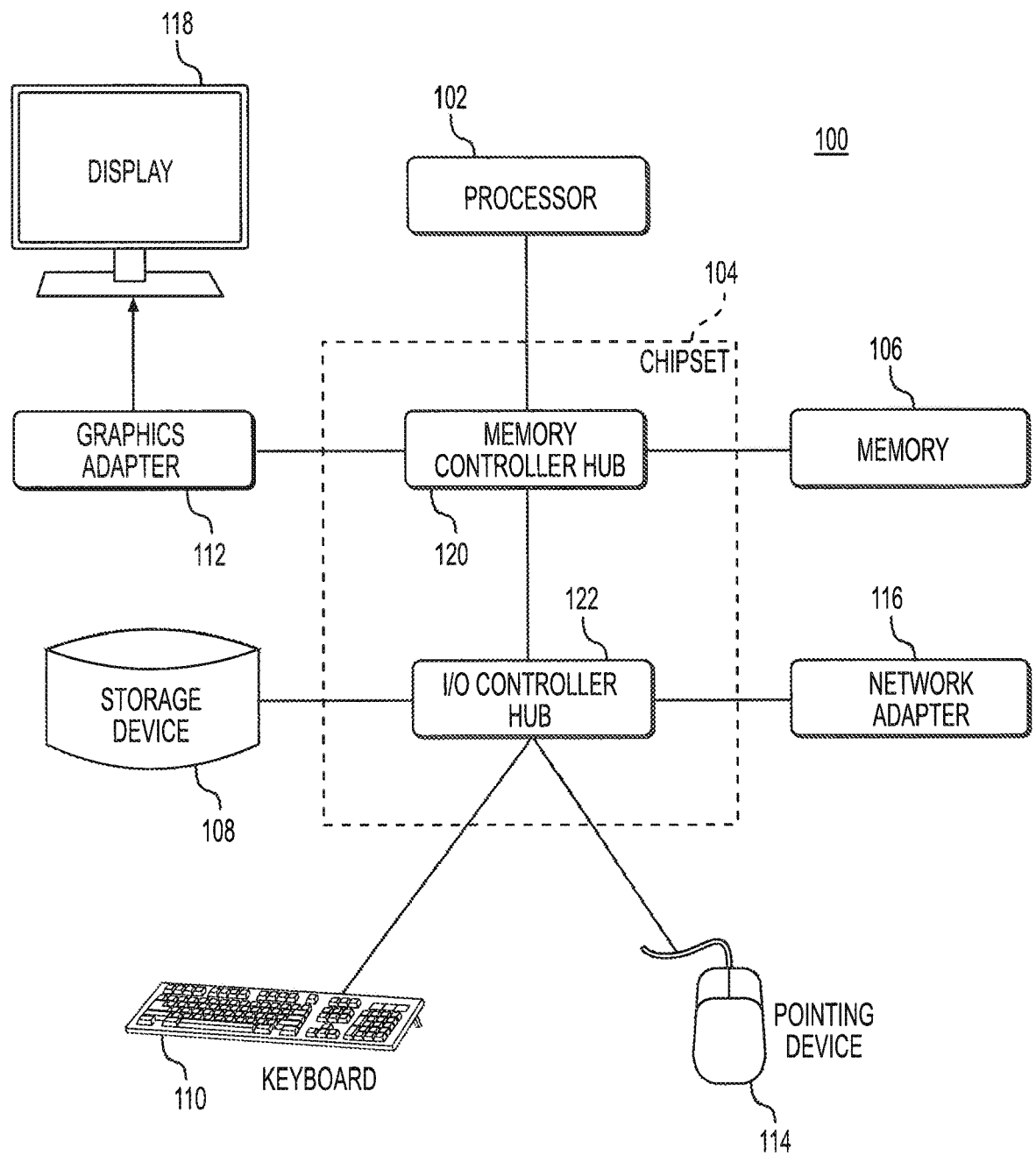
FIG. 1 is a block diagram illustrating an example computer.

FIG. 1 is a block diagram illustrating an example computer 100. The computer 100 may be any Turing machine, for example. The computer 100 includes at least one processor 102 coupled to a chipset 104. The chipset 104 includes a memory controller hub 120 and an input/output (I/O) controller hub 122. A memory 106 and a graphics adapter 112 are coupled to the memory controller hub 120, and a display 118 is coupled to the graphics adapter 112. A storage device 108, keyboard 110, pointing device 114, and network adapter 116 are coupled to the I/O controller hub 122. Other embodiments of the computer 100 may have different architectures.

The storage device 108 is a non-transitory computer-readable storage medium such as a hard drive, compact disk read-only memory (CD-ROM), DVD, or a solid-state memory device. The memory 106 holds instructions and data used by the processor 102. The pointing device 114 is a mouse, track ball, or other type of pointing device, and is used in combination with the keyboard 110 to input data into the computer 100. The pointing device 114 may also be a gaming system controller, or any type of device used to control the gaming system. For example, the pointing device 114 may be connected to a video or image capturing device that employs biometric scanning to detect a specific user. The specific user may employ motion or gestures to command the point device 114 to control various aspects of the computer 100.

The graphics adapter 112 displays images and other information on the display 118. The network adapter 116 couples the computer system 100 to one or more computer networks.

The computer 100 is adapted to execute computer program modules for providing functionality described herein. As used herein, the term "module" refers to computer program logic used to provide the specified functionality. Thus, a module can be implemented in hardware, firmware, and/or software. In one embodiment, program modules are stored on the storage device 108, loaded into the memory 106, and executed by the processor 102.

The types of computers used by the entities and processes disclosed herein can vary depending upon the embodiment and the processing power required by the entity. The computer 100 may be a mobile device, tablet, smartphone or any sort of computing element with the above-listed elements. For example, a data storage device, such as a hard disk, solid state memory or storage device, might be stored in a distributed database system comprising multiple blade servers working together to provide the functionality described herein. The computers can lack some of the components described above, such as keyboards 110, graphics adapters 112, and displays 118.

The computer 100 may act as a server (not shown). The computer 100 may be clustered with other computer 100 devices to create the server. The various computer 100 devices that constitute the server may communicate with each other over a network.

Figure 2A:
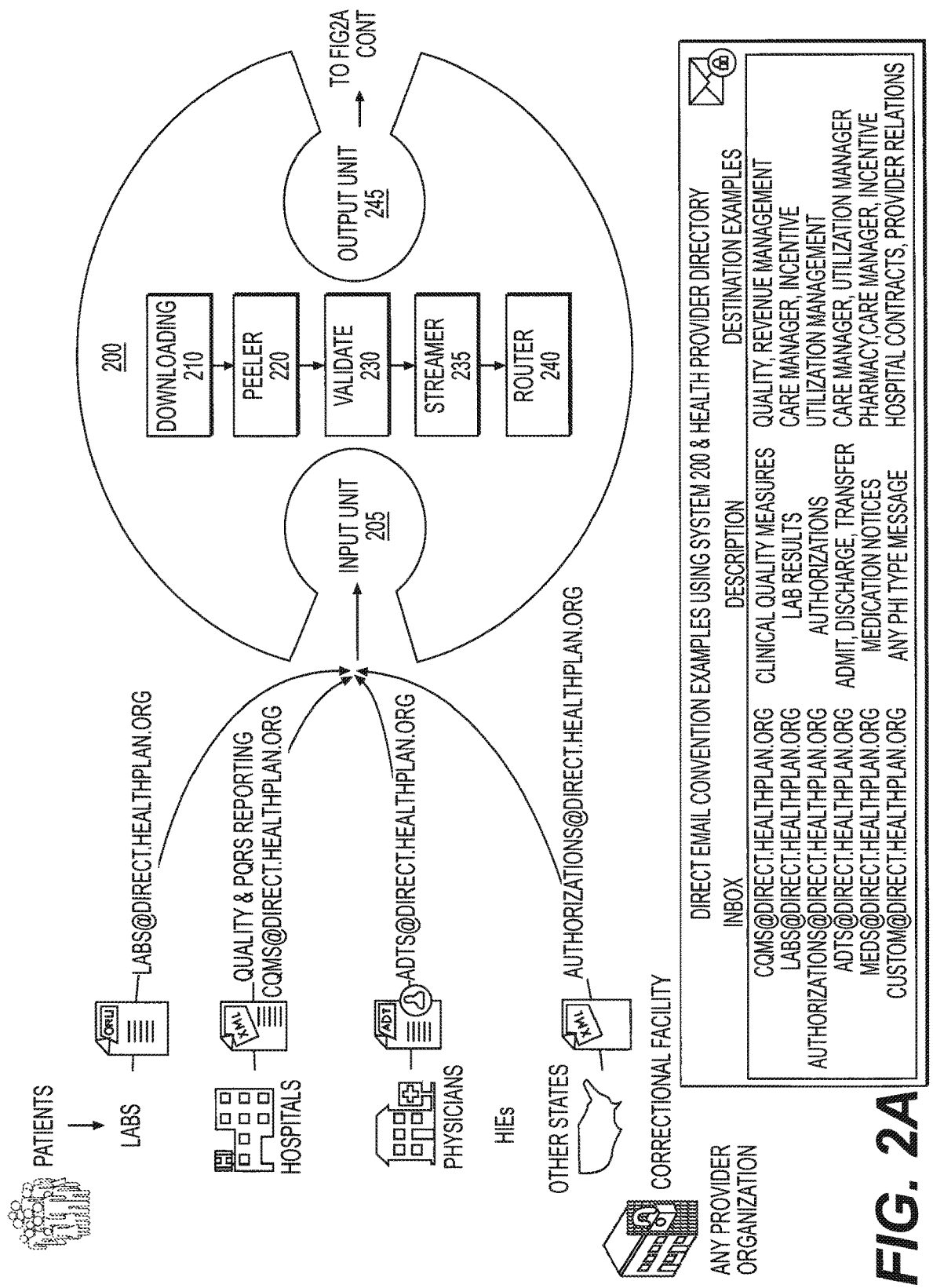
FIGS. 2(A), 2(A)-cont, 2(B), and 2(B)-cont illustrate an example of a method and system for securely transporting health information.

FIGS. 2(A) and 2(A)-cont illustrate an example of a system 200 for transforming and transporting health information for performing the method and processes described herein. The system 200 includes an input 205, a downloader 210, a transformer ("peeler") 220, a streamer 225, a validator 230, a router 240, and an output unit 245. The system 200 may be implemented on a device, such as computer 100 described above.

The system 200 receives various secured messages or secured emails from different entities, including but not limited to labs, hospitals, physicians, specialists, pharmacists, physician organizations, regional health information organizations, health information exchanges, state/local community health departments, other state health information exchanges and networks, correctional facilities, accountable care organizations, patient-centered medical homes, health plan payers (including Medicaid and Medicare), health providing entities, health care organizations, or health information sources. The entities enumerated above are involved in various facets of health care, and thus, may send or receive health information. As discussed above, each entity may be registered with a HISP (either the same HISP or multiple different HISPs), and thus, be allowed to participate in a closed system. FIG. 2(a) shows several health entities. An implementer of system 200 may use any combination of the above, or substitute those with other appropriate health providers (not shown).

The system 200 may be predefined to be associated with various identifiers shown in FIG. 2(a), such as, labs@direct.domA.org, cqms@direct.domA.org, adts@direct.domA.org, deaths@direct.domA.org or immunizations@direct.domA.org, with each of the identifiers being associated with a category or type of health information included with the secure messages sent from or to the address associated with that identifier. Thus, any time the entities listed above generate and send information pertinent to the various identifiers for the categories, such as those listed above, the entities may generate a secure message addressed to the appropriate identifier, and either manually or automatically attach the associated health information to the secure message. The associated health information attached to a single transport message may contain one or more actual records, including thousands of records combined into one attachment, such as a week's worth of immunizations or Admit-Discharge-Transfer (ADT) records saved up by a pharmacy chain or hospital and combined into one attachment to one secure message. An identifier may be a unique identification, for example, in the format of an email address, that identifies a type of service and domain to which the message is directed. An identifier may be defined as 'XXXXX@YYYYY', where XXXXX is a label for a specific type of service or category of health information, and YYYYY is a domain. For example, in response to a death occurring, a message indicating health information about the death including a county coroner's death certificate may be securely transmitted from the coroner to the deaths@direct.domA.org from which the systems and methods disclosed herein would download, detach ("peel"), stream, validate, and route the death certificate and health information to the state death records registry. One of ordinary skill in the art may appreciate that the predefined identifiers shown as part of FIG. 2(A) are merely exemplary. The implementer of system 200 may employ various conventions of identifiers typified in FIG. 2(a), excluding several of the identifiers, and adding identifiers related to other categories based on different use cases for categories of health information.

The identifiers shown in FIG. 2(A) are each specific to various categories of information. Thus, in response to health information being associated with one of the categories, the entities may communicate the health information to the input unit 205. Each entity having HISP-HISP trust with the receiver may send health information using the predefined identifiers.

The downloader 210 receives the various health information associated with the entities attached to a received message via the input unit 205. The downloader 210 may be equipped to determine the category associated with each health information item based on the identifier used to communicate to the system 200. For example, if a lab entity transmits health information to system 200, the downloader 210 may determine that the health information belongs to a lab-related category associated with the identifier.

The transformer ("peeler") 220 removes all attachments from the received message, and parses the attachments to extract all messages to be delivered to their ultimate destination. The health information downloaded by the downloader 210 may be contained in the message as an attachment containing one or more records. The transformer ("peeler") 220 may process the received health information including but not limited to parsing the information, and may extract the portion associated with the actual health information.

The transformer ("peeler") 220 may, in some embodiments, transform the received health information based on predetermined rules. Certain mandated regulations or policy concerns may dictate that health information be transformed in a specific manner, such as for ADT records that are identified as syndromics records having originated at an Emergency Department and required to be transmitted to the state syndromics surveillance system. The transformer ("peeler") 220 may be configured to determine any sort of information associated with the health information payload, and accordingly, transform the health information accordingly. Several examples of transforming information are described in detail below.

For example, If the inbound message is not HL7v2 and the routed destination is an LLP channel, the message is encapsulated into a HL7v2 message for transport to the destination system. Another example of a transformation pertains a message header routing information contained in the message conforming to the delivery requirements of the outbound systems. The transformer 220 may be configured to transform the message in accordance with rules associated with an outbound system.

The peeler 220 may optionally include the streamer 225. In certain situations, the received health information may be larger than a predetermined size. In these instances, storing and transferring the health information in a single upload/download transaction may not be wholly feasible.

In these cases, the health information may be communicated to a secondary storage device. The health information may be streamed to the secondary storage device in a streaming fashion. The streamer 225 may encrypt the health information during the streaming to ensure that there is no unencrypted personal health information stored on the secondary storage device, thereby complying with HIPAA requirements.

The validator 230 determines if the received health information is in a proper form with acceptable content to the degree possible. For example, certain types of reporting may be subject to a regulation or national standard that health information be in a certain type of format and contain certain information, such as immunization histories/forecasts as specified by the Center for Disease Control (CDC). The validator 230 may determine whether the secured message containing the health information is in a correct format and/or contains the required information that is complete. Other validations may be employed, such as verifying correct county codes. Other validations may involve advanced semantic encoding termed Logical Observation Identifier Names and Codes (LOINC)/Systemized Nomenclature of Medicine (SNOMED) codes for lab results. In response to the validator 230 determining that the health information does not satisfy the proper conditions discussed above, a message may be returned to the original source with an indication that the health information is deficient or not in the proper format. Further, information as to how to ensure the health information complies with the accepted standards and conditions may also be transmitted with the return error notification.

The validator 230 may ensure that health information is in a proper machine-readable format, such as XML, Health Level Seven (HL7), Fast Healthcare Interoperability Resources (FHIR) or any other format necessary to be processed by a receiving entity.

The validator 230 may also perform error correction on the health information. If the health information has correctable errors that make the health information not compliant with a destinations requirement, the validator 230 may address these errors. If the errors are not addressable, the validator 230 may transmit a message back to the health information's source.

The router 240 determines which party or parties are to receive the health information. The health information may be transmitted to a variety of destinations, such as public health entities (shown in FIG. 2(a)), health-care plan entities, also called "payers" (shown in FIG. 2(b)). In either case, the information of which entity, party or individual to receive the health information may be denoted in the records attached to the secure message. Thus, the router 240 may parse and analyze the health information record by record to obtain routing information for each record.

In an alternate embodiment, the router 240 may obtain additional routing information from information provided from a 'subject:' entry of an incoming message (received by the input unit 205). The information in the subject message may contain information, such as meta-data, that allows the router 240 to determine the ultimate destination of the health information.

The output unit 245 may transmit the health information transformed by system 200 to the appropriate receiving parties, whether persons, systems, or a combination of person and system endpoints. The outbound transport method may not be the same as the inbound secure messaging transport. For example, the outbound transport may be LLP over a Virtual Private Network (VPN).

Figure 3:
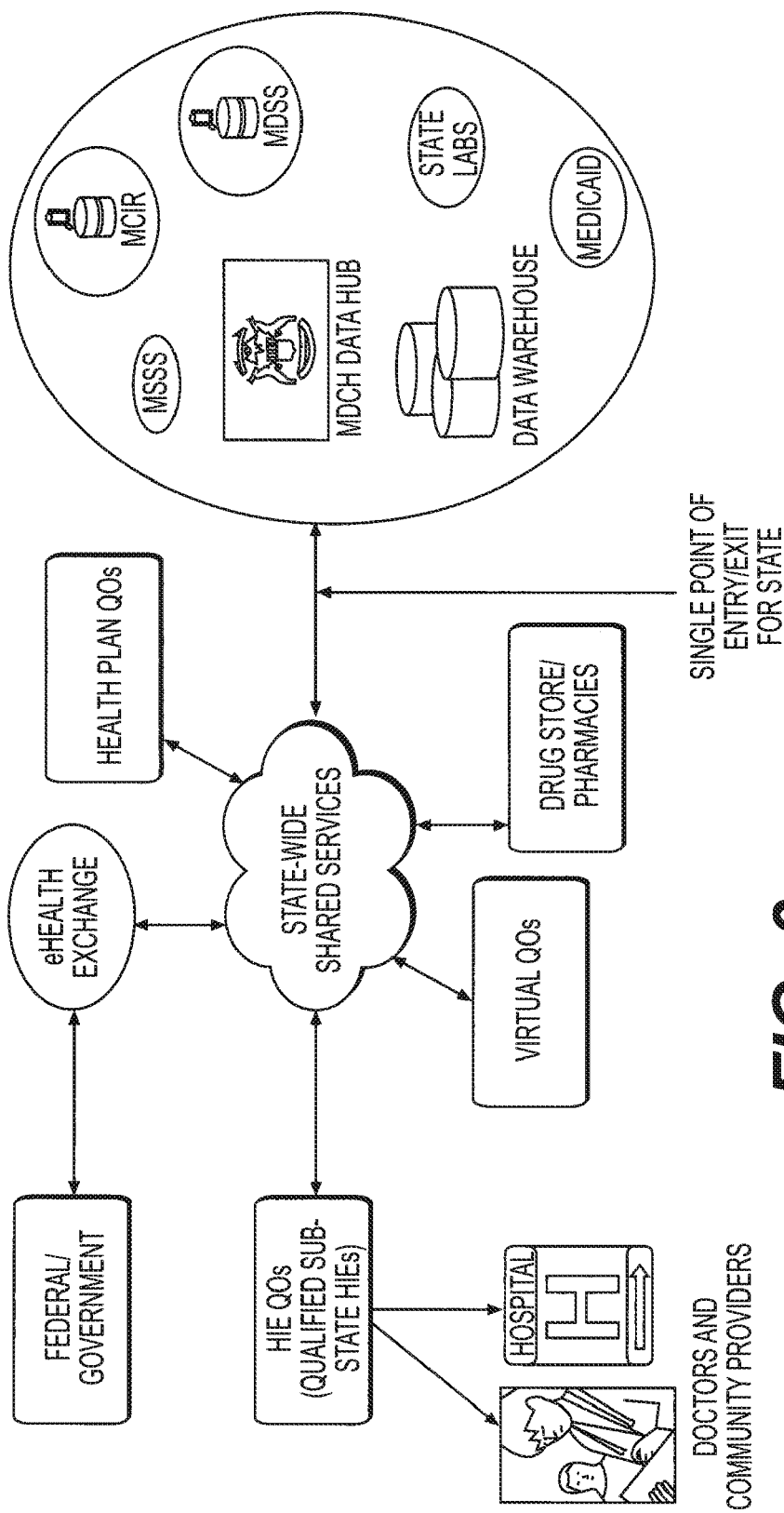
FIG. 3 illustrates an example of a report once function added to the systems described in FIGS. 2(A) and (B).

The output unit 245 may be incorporated with a report once function. FIG. 3 illustrates an example implementation of the report once functionality. In FIG. 3, various parties shown may be directed information via the output unit 245. In this way, the various parties may receive the health information in one delivery operation. In conventional implementations, the various parties are individually provided information. Thus, by providing a report once option, several steps in conventional implementations are omitted.

Also, system 200 may receive information from another state. Thus, once the information is provided from another state, system 200 may incorporate the aspects described herein to re-route the information provided from another state to an intended recipient (for example, a recipient from the other state).

As shown in FIG. 2(A), various parties may have already established a Virtual Private Network (VPN) with system 200. In the case shown in FIG. 2(A), public health entities may be auto-delivered health information that may be used by the public health entities to ascertain whether certain phenomena are occurring (e.g. syndromics) or for recording in a repository (immunization repository, disease surveillance repository, death registry, etc.) and also for attestation to meaningful use as legislated under the Affordable Care Act (ACA).

Figure 2B:
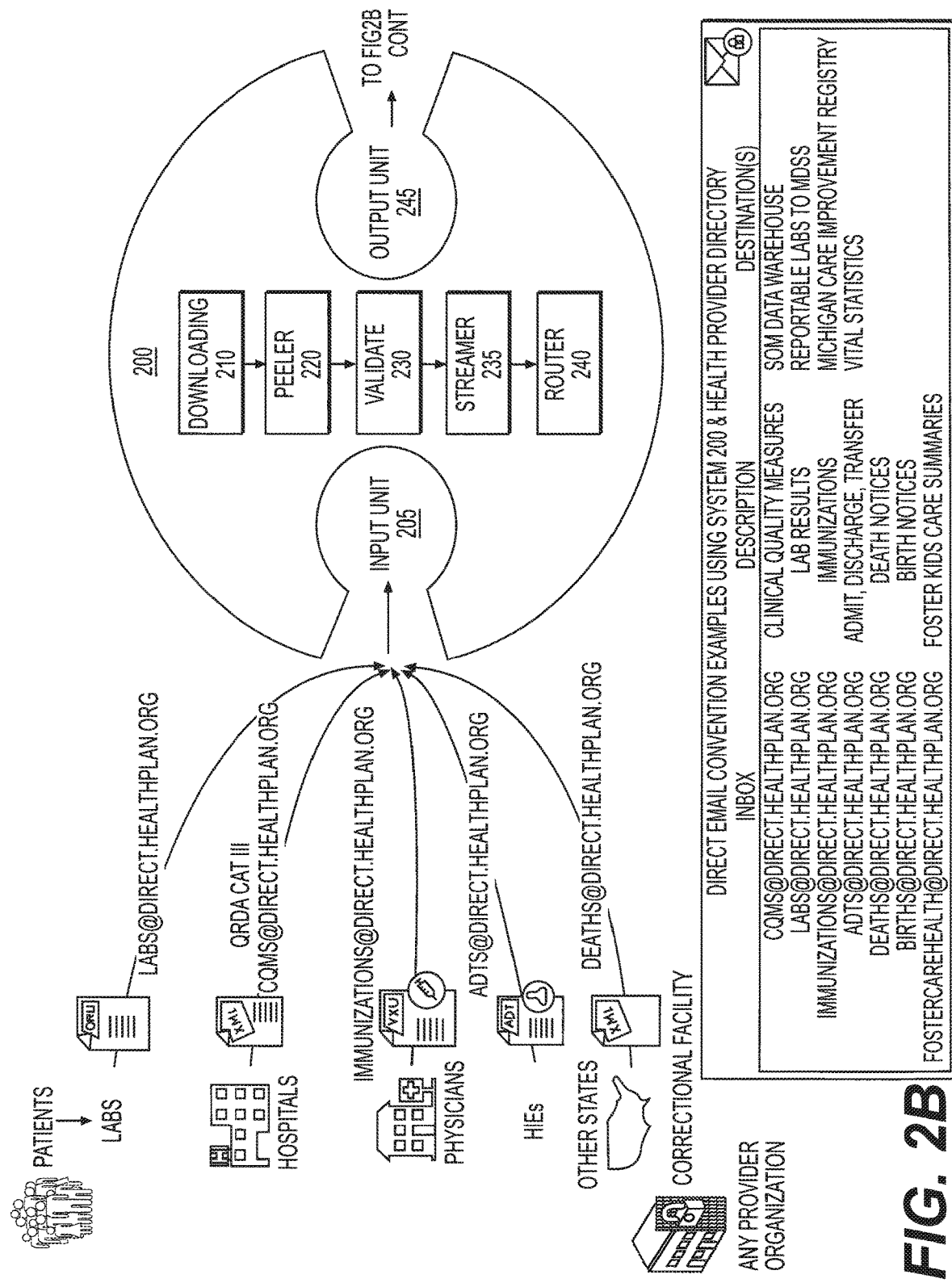

FIGS. 2(B) and 2(B)-cont illustrate an example of system 200 employed for the delivery of health information to private health plan entities, often called payers or insurers. System 200 in FIG. 2(B) is similar to the system 200 in FIG. 2(A). In FIG. 2(B), the health information is processed and routed to various recipients associated with the purchasing of health care, such as the primary care physician, members of the patient's care team, insurance providers, or the patient associated with the health information or the patient's designated patient portal or Personal Health Record (PHR) such as Microsoft HealthVault, Dossia, NoMoreClipboard, and the like.

Figure 4:
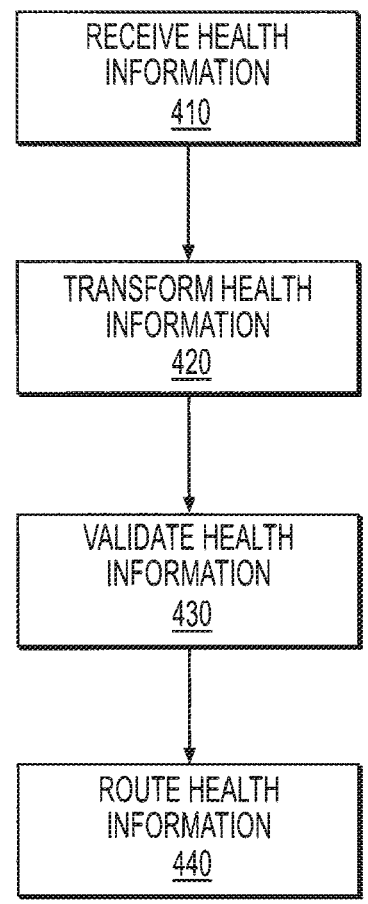
FIG. 4 illustrates an example of a method for securely transporting health information.

FIG. 4 illustrates an example method 400 for transforming and transporting health information according to an exemplary embodiment. The method 400 may be performed employing a processor as described in FIG. 1.

In operation 410, health information is received. The health information may be received by any of the sources of health information enumerated in FIGS. 2(*a*) and (*b*).

In operation 420, the health information is transformed according to predefined rules. The rules may be any sort of common health information transformation performed and known by one of ordinary skill in the art.

In operation 430, the health information may undergo a validation based on rules, such as those provided by a third-party. In the case the health information is not valid, in operation 435, a message may be initiated to return the health information to the source, with a reasoning as to why the health information may not be propagated.

In operation 440, the health information that has been transformed and validated, may be routed by a technique described above with regards to router 440. Thus, if information about the party to be routed to is included in an email address associated with the delivery of health information to a device implementing method 400, the information may be routed accordingly. Several entities which may receive the routed information are shown in FIGS. 2(*a*) and (*b*). However, the entities associated with the routing are not limited to those shown.

Certain of the devices shown in FIG. 1 include a computing system. The computing system includes a processor (CPU) and a system bus that couples various system components including a system memory such as read only memory (ROM) and random access memory (RAM), to the processor. The aspects disclosed herein may be suitably implemented on conventional computing devices, for example, computer workstations, on Internet based applications, on optical computing devices, neural computers, biological computers, molecular computing devices, and other devices. As may be appreciated by those skilled in the art, the aspects disclosed herein may be implemented on any system, automaton, and/or Turing machine.

Other system memory may be available for use as well. The computing system may include more than one processor or a group or cluster of computing system networked together to provide greater processing capability. The system bus may be any of several types of bus structures including a memory bus or memory controller, a peripheral bus, and a local bus using any of a variety of bus architectures. A basic input/output (BIOS) stored in the ROM or the like, may provide basic routines that help to transfer information between elements within the computing system, such as during start-up. The computing system further includes data stores, which maintain a database according to known database management systems. The data stores may be embodied in many forms, such as a hard disk drive, a magnetic disk drive, an optical disk drive, tape drive, or another type of computer readable media which can store data that are accessible by the processor, such as magnetic cassettes, flash memory cards, digital versatile disks, cartridges, random access memories (RAMs) and, read only memory (ROM). The data stores may be connected to the system bus by a drive interface. The data stores provide nonvolatile storage of computer readable instructions, data structures, program modules and other data for the computing system.

To enable human (and in some instances, machine) user interaction, the computing system may include an input device, such as a microphone for speech and audio, a touch sensitive screen for gesture or graphical input, keyboard, mouse, motion input, and so forth. An output device can include one or more of a number of output mechanisms. In some instances, multimodal systems enable a user to provide multiple types of input to communicate with the computing system. A communications interface generally enables the computing device system to communicate with one or more other computing devices using various communication and network protocols.

Embodiments disclosed herein can be implemented in digital electronic circuitry, or in computer software, firmware, or hardware, including the herein disclosed structures and their equivalents. Some embodiments can be implemented as one or more computer programs, i.e., one or more modules of computer program instructions, encoded on a tangible computer storage medium for execution by one or more processors. A computer storage medium can be, or can be included in, a computer-readable storage device, a computer-readable storage substrate, or a random or serial access memory. The computer storage medium can also be, or can be included in, one or more separate tangible components or media such as multiple CDs, disks, or other storage devices. The computer storage medium does not include a transitory signal.

As used herein, the term processor encompasses all kinds of apparatus, devices, and machines for processing data, including by way of example a programmable processor, a comput13r, a system on a chip, or multiple ones, or combinations, of the foregoing. The processor can include special purpose logic circuitry, e.g., an FPGA (field programmable gate array) or an ASIC (application-specific integrated circuit). The processor also can include, in addition to hardware, code that creates an execution environment for the computer program in question, e.g., code that constitutes processor firmware, a protocol stack, a database management system, an operating system, a cross-platform runtime environment, a virtual machine, or a combination of one or more of them.

A computer program (also known as a program, module, engine, software, software application, script, or code) can be written in any form of programming language, including compiled or interpreted languages, declarative or procedural languages, and the program can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

To provide for interaction with an individual, the herein disclosed embodiments can be implemented using an interactive display, such as a graphical user interface (GUI). Such GUI's may include interactive features such as pop-up or pull-down menus or lists, selection tabs, and other features that can receive human inputs.

The computing system disclosed herein can include clients and servers. A client and server are generally remote from each other and typically interact through a communications network. The relationship of client and server arises by virtue of computer programs running on the respective computers and having a client-server relationship to each other. In some embodiments, a server transmits data (e.g., an HTML page) to a client device (e.g., for purposes of displaying data to and receiving user input from a user interacting with the client device). Data generated at the client device (e.g., a result of the user interaction) can be received from the client device at the server.

The invention claimed is:

1. A method for de-identifying and transporting health information, the method comprising:
receiving, by a processor, the health information;
de-identifying, by the processor, the received health information based on at least one predetermined rule;
determining, by the processor, whether the de-identified health information is in a proper form based on a third-party standard;
when the de-identified health information is not in the proper form:
determining, by the processor, whether the de-identified health information has correctable errors to place the de-identified health information in the proper form; and
when the de-identified health information has correctable errors, error-correcting, by the processor, the de-identified health information to place the de-identified health information in the proper form;
when the de-identified health information is in the proper form, parsing, by the processor, the de-identified health information to determine an entity to receive the de-identified health information; and
streaming, by the processor, the received health information to a secondary storage device in a manner that complies with Health Information Portability and Accountability Act (HIPAA) regulations.

2. The method according to claim 1, wherein the received health information is provided via a HISP to HISP communication.

3. The method according to claim 1, wherein the third-party standard is provided via the Center for Disease Control.

4. The method according to claim 1, wherein the third-party standard is based on a Logical Observation Identifier Names and Codes standard.

5. The method according to claim 1, wherein the third-party standard is based on the Systemized Nomenclature of Medicine standard.

6. The method according to claim 1, wherein the received health information includes an identifier, and the identifier is employed to determine a category in which the received health information is associated with.

7. The method according to claim 1, further comprising, after parsing the de-identified health information, routing, by the processor, the de-identified health information to the determined entity.

8. The method according to claim 7, wherein the determined entity is a Health Plan Data Warehouse.

9. The method according to claim 7, wherein the determined entity is a personal health care provider.

10. The method according to claim 1, further comprising, when the de-identified health information is not in the proper form and has uncorrectable errors, transmitting, by the processor, a message to a source of the health information.

11. A system comprising:
data processing hardware; and
memory hardware in communication with the data processing hardware, the memory hardware storing instructions that when executed on the data processing hardware cause the data processing hardware to perform operations for de-identifying and transporting health information, the operations comprising:
receiving the health information;
de-identifying the received health information based on at least one predetermined rule;
determining whether the de-identified health information is in a proper form based on a third-party standard;
when the de-identified health information is not in the proper form:
determining whether the de-identified health information has correctable errors to place the de-identified health information in the proper form; and when the health information has correctable errors, error-correcting the received health information to place the de-identified health information in the proper form;

when the de-identified health information is in the proper form, parsing the de-identified health information to determine an entity to receive the de-identified health information; and streaming the received health information to a secondary storage device in a manner that complies with Health Information Portability and Accountability Act (HIPAA) regulations.

12. The system according to claim 11, wherein the received health information is provided via a HISP to HISP communication.

13. The system according to claim 11, wherein the third-party standard is provided via the Center for Disease Control.

14. The system according to claim 11, wherein the third-party standard is based on a Logical Observation Identifier Names and Codes standard.

15. The system according to claim 11, wherein the third-party standard is based on the Systemized Nomenclature of Medicine standard.

16. The system according to claim 11, wherein the received health information includes an identifier, and the identifier is employed to determine a category in which the received health information is associated with.

17. The system according to claim 11, wherein the operations further comprise, after parsing the de-identified health information, routing the de-identified health information to the determined entity.

18. The system according to claim 17, wherein the determined entity is a Health Plan Data Warehouse.

19. The system according to claim 17, wherein the determined entity is a personal health care provider.

20. The system according to claim 11, wherein the operations further comprise, when the de-identified health information is not in the proper form and has uncorrectable errors, transmitting a message to a source of the health information.

* * * * *